(12) United States Patent
Gouot et al.

(10) Patent No.: US 7,670,990 B2
(45) Date of Patent: Mar. 2, 2010

(54) FUNGICIDAL COMPOSITION COMPRISING A PYRIDYLETHYLBENZAMIDE DERIVATIVE AND A COMPOUND CAPABLE OF INHIBITING MITOSIS AND CELL DIVISION

(75) Inventors: Jean-Marie Gouot, St Cyr Au Mont d'Or (FR); Marie-Claire Grosjean-Cournoyer, Curis Au Mont d'Or (FR)

(73) Assignee: Bayer Cropscience S.A. (FR)

( * ) Notice: Subject to any disclaimer, the term of this patent is extended or adjusted under 35 U.S.C. 154(b) by 277 days.

(21) Appl. No.: 10/588,534

(22) PCT Filed: Feb. 10, 2005

(86) PCT No.: PCT/EP2005/002565

§ 371 (c)(1), (2), (4) Date: Oct. 12, 2006

(87) PCT Pub. No.: WO2005/077180

PCT Pub. Date: Aug. 25, 2005

(65) Prior Publication Data
US 2008/0026942 A1    Jan. 31, 2008

Related U.S. Application Data

(60) Provisional application No. 60/636,954, filed on Dec. 17, 2004.

(30) Foreign Application Priority Data
Feb. 12, 2004   (EP)  .................... 04356018

(51) Int. Cl.
*A01N 47/10* (2006.01)
*A01N 55/02* (2006.01)
*A01N 43/40* (2006.01)
*A01N 43/64* (2006.01)
*A61K 31/44* (2006.01)
*C07D 213/56* (2006.01)

(52) U.S. Cl. ............... 504/135; 504/126; 504/130; 504/133; 514/357; 546/336

(58) Field of Classification Search ............... 504/130, 504/126, 133, 135; 514/357; 546/336
See application file for complete search history.

(56) References Cited

U.S. PATENT DOCUMENTS

| 2,899,437 | A | * | 8/1959 | Shapiro et al. | ............ 546/337 |
| 3,954,993 | A | * | 5/1976 | Pommer et al. | ............ 514/533 |
| 4,835,169 | A | * | 5/1989 | Wiedmer | ............ 514/383 |
| 5,532,262 | A | * | 7/1996 | Brandes et al. | ............ 514/388 |
| 2005/0234110 | A1 | * | 10/2005 | Mansfield et al. | ............ 514/357 |

FOREIGN PATENT DOCUMENTS

| WO | WO9942447 | * | 8/1999 |
| WO | WO 01/11965 |   | 2/2001 |

OTHER PUBLICATIONS

Hammond, L., Exploring the mechanisms of action of FB642 at the cellular level, 2001, J Cancer Res Clin Oncol, Springer-Verlag, 124:301-313.*
S.R. Colby, *Weeds*, "Calculating Synergistic and Antagonistic Responses of Herbicide Combinations", (1967), 15, pp. 20-22.

* cited by examiner

*Primary Examiner*—Johann R Richter
*Assistant Examiner*—Danielle Sullivan
(74) *Attorney, Agent, or Firm*—Ostrolenk Faber LLP

(57) ABSTRACT

A composition comprising at least a pyridylethylbenzamide derivative of general formula (I) (a) and a compound capable of inhibiting mitosis and cell division (b) in a (a)/(b) weight ratio of from 0.01 to 20.

A composition further comprising an additional fungicidal compound.

A method for preventively or curatively combating the phytopathogenic fungi of crops by using this composition.

19 Claims, No Drawings

FUNGICIDAL COMPOSITION COMPRISING A PYRIDYLETHYLBENZAMIDE DERIVATIVE AND A COMPOUND CAPABLE OF INHIBITING MITOSIS AND CELL DIVISION

CROSS-REFERENCE TO RELATED APPLICATIONS

The present application is a 35 U.S.C. §371 national phase conversion of PCT/EP2005/002565 filed Feb. 10, 2005, which claims priority of EP Application No. 04356018.4 filed Feb. 12, 2004, and U.S. Provisional Application No. 60/636,954 filed Dec. 17, 2004.

The present invention relates to novel fungicide compositions comprising a pyridylethylbenzamide derivative and a compound capable of inhibiting mitosis and cell division. The present invention also relates to a method of combating or controlling phytopathogenic fungi by applying at a locus infested or liable to be infested such a composition.

International patent application WO 01/11965 generically discloses numerous pyridylethylbenzamide derivatives. The possibility of combining one or more of these numerous pyridylethylbenzamide derivatives with known fungicidal products to develop a fungicidal activity is disclosed in general terms, without any specific example or biological data.

It is always of high-interest in agriculture to use novel pesticidal mixtures showing a synergistic effect in order notably to avoid or to control the development of resistant strains to the active ingredients or to the mixtures of known active ingredients used by the farmer while minimising the doses of chemical products spread in the environment and reducing the cost of the treatment.

We have now found some novel fungicidal compositions which possess the above mentioned characteristics.

Accordingly, the present invention relates to a composition comprising:
a) a pyridylethylbenzamide derivative of general formula (I)

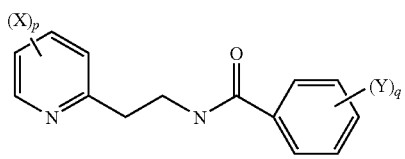

(I)

in which:
p is an integer equal to 1, 2, 3 or 4;
q is an integer equal to 1, 2, 3, 4 or 5;
each substituent X is chosen, independently of the others, as being halogen, alkyl or haloalkyl;
each substituent Y is chosen, independently of the others, as being halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkylsulphonyl, phenylsulphonyl or benzylsulphonyl;
as to the N-oxides of 2-pyridine thereof;

and
b) a compound capable of inhibiting mitosis and cell division;
in a (a)/(b) weight ratio of from 0.01 to 20.

In the context of the present invention:
halogen means chlorine, bromine, iodine or fluorine;
each of the alkyl or acyl radicals present in the molecule contains from 1 to 10 carbon atoms, preferably from 1 to 7 carbon atoms, more preferably from 1 to 5 carbon atoms, and may be linear or branched;
each of the alkenyl or alkynyl radicals present in the molecule contains from 2 to 10 carbon atoms, preferably from 2 to 7 carbon atoms, more preferably from 2 to 5 carbon atoms, and may be linear or branched.

The composition according to the present invention provides a synergistic effect. This synergistic effect allows a reduction of the chemical substances spread into the environment and a reduction of the cost of the fungal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x*y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The composition according to the present invention comprises a pyridylethylbenzamide derivative of general formula (I). Preferably, the present invention relates to a composition comprising a pyridylethylbenzamide derivative of general formula (I) in which the different characteristics may be chosen alone or in combination as being:
as regards p, p is 2;
as regards q, q is 1 or 2. More preferably, q is 2;
as regards X, X is chosen, independently of the others, as being halogen or haloalkyl. More preferably, X is chosen, independently of the others, as being a chlorine atom or a trifluoromethyl group;
as regards Y, Y is chosen, independently of the others, as being halogen or haloalkyl. More preferably, Y is chosen, independently of the others, as being a chlorine atom or a trifluoromethyl group;

More preferably, the pyridylethylbenzamide derivative of general formula (I) present in the composition of the present invention is:
N-{2-[3-chloro-5-(trifluoromethyl)-2-pyridinyl]ethyl}-2-trifluoromethylbenzamide (compound 1);
N-{2-[3-chloro-5-(trifluoromethyl)-2-pyridinyl]ethyl}-2-iodobenzamide (compound 2); or
N-{2-[3,5-dichloro-2-pyridinyl]ethyl}-2-trifluoromethylbenzamide (compound 3).

Even more preferably, the pyridylethylbenzamide derivative of general formula (I) present in the composition of the present invention is N-{2-[3-chloro-5-(trifluoromethyl)-2-pyridinyl]ethyl}-2-trifluoromethylbenzamide (compound 1).

The composition according to the present invention comprises a compound capable of inhibiting mitosis and cell division. Preferably, the present invention relates to a composition comprising a compound capable of inhibiting mitosis and cell division selected from [5-Chloro-6-(2,4,6-trifluoro-phenyl)-[1,2,4]triazolo[1,5-α]pyrimidin-7-yl]-((R)-1, 2,2-trimethyl-propyl)-amine, [5-Chloro-6-(2,4,6-trifluoro-phenyl)-[1,2,4]triazolo[1,5-α]pyrimidin-7-yl]-((R)-1,2-dimethyl-propyl)-amine, 5-Chloro-7-(4-methyl-piperidin-1-yl)-6-(2,4,6-trifluoro-phenyl)-[1,2,4]triazolo[1,5-α]pyrimidine, benzimidazole derivatives, thiophanate, thiophanate-methyl, diethofencarb, zoxamide or pencycuron.

According to the present invention, benzimidazole derivatives may for example be benomyl, carbendazim, fuberidazole or thiabendazole.

The composition according to the present invention comprises (a) at least a pyridylethylbenzamide derivative of general formula (I) and (b) a compound capable of inhibiting mitosis and cell division in an (a)/(b) weight ratio of from 0.01 to 20; preferably of from 0.05 to 10; even more preferably, of from 0.1 to 5.

The composition of the present invention may further comprise at least one other different fungicide active ingredient (c).

The fungicidal active ingredient (c) may be selected from azaconazole, azoxystrobin, (Z)-N-[α-(cyclopropylmethoxyimino)-2,3-difluoro-6-(trifluoromethyl)benzyl]-2-phenylacetamide, benalaxyl, benomyl, benthiavalicarb, biphenyl, bitertanol, blasticidin-S, boscalid, borax, bromuconazole, bupirimate, sec-butylamine, calcium polysulfide, captafol, captan, carbendazim, carboxin, carpropamid, chinomethionat, chlorothalonil, chlozolinate, copper hydroxide, copper octanoate, copper oxychloride, copper sulfate, cuprous oxide, cyazofamid, cymoxanil, cyproconazole, cyprodinil, dazomet, debacarb, dichlofluanid, dichlorophen, diclobutrazole, diclocymet, diclomezine, dicloran, diethofencarb, difenoconazole, difenzoquat metilsulfate, difenzoquat, diflumetorim, dimethirimol, dimethomorph, diniconazole, dinobuton, dinocap, diphenylamine, dithianon, dodemorph, dodemorph acetate, dodine, edifenphos, epoxiconazole, etaconazole, ethaboxam, ethirimol, ethoxyquin, etridiazole, famoxadone, fenamidone, fenarimol, fenbuconazole, fenfuram, fenhexamid, fenpiclonil, fenoxanil, fenpropidin, fenpropimorph, fentin, fentin hydroxide, fentin acetate, ferbam, ferimzone, fluazinam, fludioxonil, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, hexachlorobenzene, hexaconazole, 8-hydroxyquinoline sulfate, potassium hydroxyquinoline sulfate, hymexazol, imazalil sulfate, imazalil, imibenconazole, iminoctadine, iminoctadine triacetate, ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, metalaxyl-M, metam-sodium, metam, metconazole, methasulfocarb, methyl isothiocyanate, metiram, metominostrobin, mildiomycin, myclobutanil, nabarn, nickel bis(dimethyldithiocarbamate), nitrothal-isopropyl, nuarimol, octhilinone, ofurace, oleic acid, oxadixyl, oxine-copper, oxpoconazole fumarate, oxycarboxin, pefurazoate, penconazole, pencycuron, pentachlorophenol, sodium pentachlorophenoxide, pentachlorophenyl laurate, phenylmercury acetate, sodium 2-phenylphenoxide, 2-phenylphenol, phosphorous acid, phthalide, picoxystrobin, piperalin, polyoxinspolyoxin B, polyoxin, polyoxorim, probenazole, prochloraz, procymidone, propamocarb hydrochloride, propamocarb, propiconazole, propineb, prothioconazole, pyraclostrobin, pyrazophos, pyributicarb, pyrifenox, pyrimethanil, pyroquilon, quinoxyfen, quintozene, silthiofam, simeconazole, spiroxamine, sulfur, tar oils, tebuconazole, tecnazene, tetraconazole, thiabendazole, thifluzamide, thiophanate-methyl, thiram, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram and, zoxamide.

Preferably, third fungicidal active ingredient (c) is selected from iprodione and chlorotalonil.

Where the third active ingredient (c) as defined above is present in the composition, this compound may be present in an amount of (a):(b):(c) weight ratio of from 1:0.01:0.01 to 1:20:20; the ratios of compound (a) and compound (c) varying independently from each other. Preferably, the (a):(b):(c) weight ratio may be of from 1:0.05:0.05 to 1:10:10.

Following compositions may be cited to illustrate in a non-limited manner the present invention: compound 1 with [5-Chloro-6-(2,4,6-trifluoro-phenyl)-[1,2,4]triazolo[1,5-a]pyrimidin-7-yl]-((R)-1,2,2-trimethyl-propyl)-amine, compound 1 with [5-Chloro-6-(2,4,6-trifluoro-phenyl)-[1,2,4]triazolo[1,5-a]pyrimidin-7-yl]-((R)-1,2-dimethyl-propyl)-amine, compound 1 with 5-Chloro-7-(4-methyl-piperidin-1-yl)-6-(2,4,6-trifluoro-phenyl)-[1,2,4]triazolo[1,5-a]pyrimidine, compound 1 with thiophanate, compound 1 with thiophanate-methyl, compound 1 with diethofencarb, compound 1 with zoxamide, compound 1 with pencycuron, compound 1 with benomyl, compound 1 with carbendazim, compound 1 with fuberidazole, compound 1 with thiabendazole, compound 2 with [5-Chloro-6-(2,4,6-trifluoro-phenyl)-[1,2,4]triazolo[1,5-α]pyrimidin-7-yl]-((R)-1,2,2-trimethyl-propyl)-amine, compound 2 with [5-Chloro-6-(2,4,6-trifluoro-phenyl)-[1,2,4]triazolo[1,5-a]pyrimidin-7-yl]-((R)-1,2-dimethyl-propyl)-amine, compound 2 with 5-Chloro-7-(4-methyl-piperidin-1-yl)-6-(2,4,6-trifluoro-phenyl)-[1,2,4]triazolo[1,5-a]pyrimidine, compound 2 with thiophanate, compound 2 with thiophanate-methyl, compound 2 with diethofencarb, compound 2 with zoxamide, compound 2 with pencycuron, compound 2 with benomyl, compound 2 with carbendazim, compound 2 with fuberidazole, compound 2 with thiabendazole, compound 3 with [5-Chloro-6-(2,4,6-trifluoro-phenyl)-[1,2,4]triazolo[1,5-a]pyrimidin-7-yl]-((R)-1,2,2-trimethyl-propyl)-amine, compound 3 with [5-Chloro-6-(2,4,6-trifluoro-phenyl)-[1,2,4]triazolo[1,5-a]pyrimidin-7-yl]-((R)-1,2-dimethyl-propyl)-amine, compound 3 with 5-Chloro-7-(4-methyl-piperidin-1-yl)-6-(2,4,6-trifluoro-phenyl)-[1,2,4]triazolo[1,5-a]pyrimidine, compound 3 with thiophanate, compound 3 with thiophanate-methyl, compound 3 with diethofencarb, compound 3 with zoxamide, compound 3 with pencycuron, compound 3 with benomyl, compound 3 with carbendazim, compound 3 with fuberidazole, compound 3 with thiabendazole.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10% to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The fungicidal compositions of the present invention can be used to curatively or preventively control phytopathogenic fungi of crops. Thus, according to a further aspect of the present invention, there is provided a method for preventively or curatively controlling phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated or controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma* specie *tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma* specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., *Trichoderma* sp., *Aspergillus* sp., *and Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium* sp.);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae; M. laxa*), scab (*Venturia inaequalis*), powdery mildew (*Podosphaera leucotricha*);

vine, as regards diseases of the foliage: in particular grey mould (*Botrylis cinerea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

The fungicidal composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The fungicidal composition according to the present invention may also be used in the treatment of genetically modified organisms with the compounds according to the invention or the agrochemical compositions according to the invention. Genetically modified plants are plants into in which genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The dose of active material usually applied in the treatment according to the present invention is generally and advantageously between 10 and 2000 g/ha, preferably between 20 and 1500 g/ha for applications in foliar treatment. The dose of active substance applied is generally and advantageously between 1 and 200 g per 100 kg of seed, preferably between 2 and 150 g per 100 kg of seed in the case of seed treatment. It is clearly understood that the doses indicated above are given as illustrative examples of the invention. A person skilled in the art will know how to adapt the application doses according to the nature of the crop to be treated.

The compositions according to the present invention may also be used fore the preparation of composition useful to curatively or preventively treat human and animal fungal diseases such as, for example, mycoses, dermatoses, trichophyton diseases and candidiases or diseases caused by *Aspergillus* spp. or *Candida* spp., for example *Aspergillus fumigatus* or *Candida albicans* respectively.

The present invention will now be illustrated with the following example:

EXAMPLE 1

Efficacy Against *Erysiphe graminis* f. sp. *tritici* of a Composition Containing N-{2-[3-chloro-5-(trifluoromethyl)-2-pyridinyl]ethyl}-2-trifluoromethylbenzamide (Compound 1) and Carbendazim The active ingredients tested are prepared by potter homogenisation in a mixture of acetone/tween/water. This suspension is then diluted with water to obtain the desired active material concentration.

Wheat plants (*Audace* variety) in starter cups, sown on 50/50 peat soil-pozzolana substrate and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by dusting them with *Erysiphe graminis* f. sp. *tritici* spores, the dusting being carried out using diseased plants.

Grading is carried out 7 to 14 days after the contamination, in comparison with the control plants.

The following table summarises the results obtained when tested compound 1 and carbendazim alone and in a 1:1 weight ratio mixture.

|  | Dose (g/ha) | % Efficacy | Synergism (Colby) |
|---|---|---|---|
| Compound 1 | 62.5 | 42 | — |
|  | 125 | 63 | — |
| Carbendazim | 62.5 | 0 | — |
|  | 125 | 16 | — |
| Compound 1 + carbendazim (Ratio 1:1) | 62.5 + 62.5 | 53 | +11 |
|  | 125 + 125 | 79 | +10 |

According to the Colby method, a synergistic effect of the mixtures tested has been observed.

The invention claimed is:

1. A composition comprising:
   (a) a pyridylethylbenzamide derivative of general formula (I)

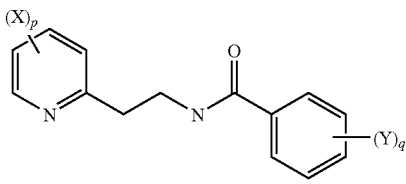

in which:
p is an integer equal to 1, 2, 3 or 4;
q is an integer equal to 1, 2, 3, 4 or 5;
each substituent X is chosen, independently of the others, as being halogen, alkyl or haloalkyl;
each substituent Y is chosen, independently of the others, as being halogen, alkyl, or haloalkyl;
as to the N-oxides of 2-pyridine thereof; and
(b) a compound capable of inhibiting mitosis and cell division selected from the group consisting of benzimidazole derivatives;
in an (a)/(b) weight ratio of from 0.01 to 20.

2. The composition of claim 1 wherein p is 2.

3. The composition of claim 1 wherein q is 2.

4. The composition of claim 1 wherein each X is independently selected from the group consisting of halogen and haloalkyl.

5. The composition of claim 1 wherein each X is independently selected from the group consisting of a chlorine atom and a trifluoromethyl group.

6. The composition of claim 1 wherein each Y is independently selected from the group consisting of halogen and haloalkyl.

7. The composition of claim 1 wherein each Y is independently selected from the group consisting of a chlorine atom and a trifluoromethyl group.

8. The composition of claim 1 wherein the compound of general formula (I) is selected from the group consisting of:
N-{2-[3-chloro-5-(trifluoromethyl)-2-pyridinyl]ethyl}-2-trifluoromethylbenzamide;
N-{2-[3-chloro-5-(trifluoromethyl)-2-pyridinyl]ethyl}-2-iodobenzamide; and
N-{2-[3,5-dichloro-2-pyridinyl]ethyl}-2-trifluoromethylbenzamide.

9. The composition of claim 8 wherein the compound of general formula (I) is
N-{2-[3-chloro-5-(trifluoromethyl)-2-pyridinyl]ethyl}-2-trifluoromethylbenzamide.

10. The composition of claim 1 wherein the benzimidazole derivative is selected from the group consisting of benomyl, carbendazim, fuberidazole and thiabendazole.

11. The composition of claim 1 further comprising a fungicidal compound (c).

12. The composition of claim 11 wherein the fungicidal compound (c) is selected from the group consisting of iprodione and chlorothalonil.

13. A composition comprising:
(a) N-{2-[3-chloro-5-(trifluoromethyl)-2-pyridinyl]ethyl}-2-trifluoromethylbenzamide; and
(b) a compound capable of inhibiting mitosis and cell division selected from the group consisting of benomyl, carbendazim, fuberidazole and thiabendazole;
in an (a)/(b) weight ratio of from 0.01 to 20.

14. The composition of claim 13 further comprising an agriculturally acceptable support, carrier, filler and/or surfactant.

15. A method for preventively or curatively controlling phytopathogenic fungi of crops comprising applying an effective and non-phytotoxic amount of a composition according claim 13 to the seed, the plant and/or to the fruit of the plant or to the soil in which the plant is growing or in which it is desired to grow.

16. The composition of claim 13 wherein (b) is carbendazim.

17. The composition of claim 13 further comprising a fungicidal compound (c) selected from the group consisting of iprodione and chlorothalonil.

18. The composition of claim 16 in an (a)/(b) weight ratio of 1:1.

19. The composition of claim 16 further comprising a fungicidal compound (c) selected from the group consisting of iprodione and chlorothalonil.

* * * * *